United States Patent
Kostrzewa et al.

(10) Patent No.: US 6,589,735 B1
(45) Date of Patent: Jul. 8, 2003

(54) SIMPLE SNP ANALYSIS USING MASS SPECTROMETRY

(75) Inventors: Markus Kostrzewa, Panitzsch (DE); Thomas Fröhlich, Leipzig (DE); Thomas Wenzel, Leipzig (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 09/434,557

(22) Filed: Nov. 12, 1999

(30) Foreign Application Priority Data

Dec. 11, 1998 (DE) .......................... 198 52 167

(51) Int. Cl.[7] .............. C12Q 1/68; C12P 19/34
(52) U.S. Cl. ............. 435/6; 435/91.1; 435/91.2; 536/22.1; 536/25.3
(58) Field of Search .............. 435/6, 91.1, 91.2; 536/22.1, 25.3

(56) References Cited

U.S. PATENT DOCUMENTS 5,965,363 A * 10/1999 Monforte et al. .............. 435/6
6,090,558 A    7/2000 Butler et al. ................. 435/6

FOREIGN PATENT DOCUMENTS

WO   WO 97/33000 A1   9/1997
WO   WO 99/14375 A2   3/1999

OTHER PUBLICATIONS

Daniel P. Little et al.; Detection of RET proto–oncogene codon 634 mutations using mass spectrometry; J Mol Med (1997) 75:745–750.

* cited by examiner

*Primary Examiner*—Jezia Riley

(57) ABSTRACT

The invention relates to a method of investigating by mass spectrometry the genetic material deoxyribonucleic acid (DNA) replicated by polymerase chain reaction (PCR), for the identification of known mutations and polymorphisms; it particularly relates to the analysis of single nucleotide polymorphisms (SNPs) by matrix assisted laser desorption and ionization (MALDI).

The invention consists of using a set of nucleoside triphosphates for the selective PCR replication of the DNA in which one or more of the nucleoside triphosphates have been made much heavier by attaching a chemical group, but in such a way that the replication is not disturbed by the polymerase. In this way a single nucleotide polymorphism in DNA pieces with a length of about 40 to 50 bases can very easily be made visible by mass spectrometry without any further manipulation.

9 Claims, 2 Drawing Sheets

M = -$P_3O_9H_4$, -$P_3O_8SH_4$
Q = O, S
X = -R, -$(CH_2)_n$-R, -C≡C-R
R = -H, -F, -Cl, -Br, -I, -OH, -SH, -SeH, -Alkyl, -Alkenyl, -Alkinyl, -$OCH_3$, -$SCH_3$,
  -$(OCH_2CH_2)_n$-O-Alkyl, -$NH_2$, -$(NHCOCH_2)_n$-$NH_2$,
  -$(NHCOCHCH_3)_n$-$NH_2$, -$OCOCH_2NH_2$, -$OCOCH_2(NHCOCH_2)_n$-
   $NH_2$, -$OCOCHCH_3NH_2$, -$OCOCHCH_3(NHCOCH_3)_n$-$NH_2$, -$CHF_2$, -$CF_3$,
   -$OCH_2F$, -$OCHF_2$, -$OCF_3$, -$SCH_2F$, -$SCHF_2$, -$SeCH_3$
Y = CH, N
Z = O, S, Se

SIMPLE SNP ANALYSIS USING MASS SPECTROMETRY

The invention relates to a method of investigating by mass spectrometry the genetic material deoxyribonucleic acid (DNA) replicated by polymerase chain reaction (PCR), for the identification of known mutations and polymorphisms; it particularly relates to the analysis of single nucleotide polymorphisms (SNPs) by matrix assisted laser desorption and ionization (MALDI).

The invention consists of using a set of nucleoside triphosphates for the selective PCR replication of the DNA in which one or more of the nucleoside triphosphates have been made much heavier by attaching a chemical group, but in such a way that the replication is not disturbed by the polymerase. In this way a single nucleotide polymorphism in DNA pieces with a length of about 40 to 50 bases can very easily be made visible by mass spectrometry without any further manipulation.

BACKGROUND OF THE INVENTION

Subject of this invention is a method for easily and quickly detecting mutative changes at certain known points of the genomic DNA of an organism. Special consideration is here given to polymorphisms where with a statistical frequency a single base exchange is to be found at a certain point in the genome. This type of polymorphism has in recent years been given the designation "single nucleotide polymorphism" (SNP).

SNPs have in the meantime acquired considerable importance for genotyping. It is assumed that the human genome contains about 3 million such SNPs. Therefore there are about 3 million points at which with a statistical frequency a base is exchanged for a different base. Such a base exchange can take place within a gene or in non expressed areas between the genes. Therefore, and due to the large redundancy of the genetic code, an SNP can be without any phenotypical effect. Certain forms (so-called alleles) of SNPs can, however, also be linked to a phenotypical variation, e.g. by the exchange of an amino acid in a protein, by a change in the gene expression or its regulation etc. The phenotypical variation can, for example, be expressed in a changed tolerance to environmental influences, a changed pharmaceutical effect, or, under extreme circumstances, in a genetically conditioned disease. SNPs inherit half from the father and half from the mother so SNPs can also be applied in individual analysis (genetic passport).

SNPs acquire increasing importance for genotyping and particularly for the coupling analysis of multicausal diseases. The higher frequency in the genome and the thus possible denser marker network, as well as the lower mutation rate compared with the STR markers (short tandem repeats) used to date represent a considerable advantage.

The basis for detecting such and other mutations is the selective PCR (polymerase chain reaction), a replication method for DNA pieces in the test tube, which was only developed by K. B. Mullis in 1983 (who was awarded the Nobel Prize for it in 1993) and after introduction of temperature-stable polymerases began an unprecedented march to victory through the genetic laboratories.

PCR is the targeted replication of a piece of the double-stranded DNA (dsDNA) accurately selected by the replication method itself. Selection of the DNA segment is performed by a pair of so-called primers, two single-stranded DNA pieces (ssDNA) each having a length of about 20 nucleotides, which (described somewhat briefly and simplified) hybridize at both ends (the future ends) of the selected DNA piece. Enzymatic replication is performed by a DNA polymerase, which represents a chemical factory inside a molecule, by passing through a simple temperature cycle. The PCR reaction takes place in aqueous solution in which a few molecules of the original DNA and sufficient quantities of DNA polymerase, primers, nucleoside triphosphates, activators, and stabilizers are present. In each thermal cycle (for example the melting of the double helix at 94° C., hybridization of the primers at 55° C., reconstitution to a double helix by attachment of new DNA building blocks by the polymerase at 72° C.) the number of selected DNA segments is basically doubled. Therefore, in 30 cycles, around 1 billion DNA segments are generated from one single double strand of the DNA as original material. (In a more exact description, both primers hybridize on the two different single strands of the DNA and the shortening to the selected DNA segment including the two attached primers only occurs statistically during further replication).

Mass spectrometry with ionization of heavy molecules either by matrix-assisted laser desorption (MALDI) or by electrospray (ESI) is a very efficient method of analyzing biomolecules. For instance, the ions can be analyzed with regard to their mass in time-of-flight mass spectrometers. Since the flight velocity of the ions in the mass spectrometer is about $10^7$ faster than the migration velocity of the molecules in the gel of electrophoresis, the mass spectrometry method is exceptionally faster than the previously used gel electrophoresis method, even if the spectrum measurement is repeated 10 to 100 times in order to achieve a good signal-to-noise ratio.

Due to the capability of a higher sample throughput the MALDI method has become more widespread than ESI for analyzing DNA. The MALDI method consists of first embedding the analyte molecules on a sample support in a UV-absorbing matrix, usually an organic acid. The sample support is introduced to the ion source of a mass spectrometer. Due to a short UV laser pulse of about 3 nanoseconds in length the matrix is evaporated into the vacuum; largely unfragmented, the analyte molecule is transported into the gaseous phase. Ionization of the analyte molecule is achieved by collisions with matrix ions forming simultaneously. An applied voltage accelerates the ions into a field-free flight tube. Based on their various masses the ions in the ion source are accelerated to various velocities. Smaller ions reach the detector earlier than large ones. The time of flight is converted to the mass of the ions.

Technical innovations in hardware have significantly improved the method of time-of-flight mass spectrometry with MALDI ionization. Worth mentioning is the delayed acceleration (Delayed Extraction) with which an improved resolution of the signals is achieved at a point in the spectrum, but also an even more reduced fragmentation. By means of an additional dynamic change in acceleration voltage it is possible to achieve a good resolution in a large mass range (for example see DE 196 38 577).

Naturally the MALDI method of ionization can be also coupled to other types of mass spectrometry such as RF quadrupole ion traps or ion cyclotron resonance spectrometers.

MALDI is ideally suitable for analyzing peptides and proteins. The analysis of nucleic acids is much more difficult. For nucleic acids ionization in the MALDI process is about 100 times lower than for peptides and decreases disproportionately with increasing mass. On the one hand, DNA pieces are very fragile and easily decompose in the MALDI process, while on the other hand they tend to form adducts with numerous alkali ions. Both processes of fragmentation and adduct formation cause the determination of mass to become increasingly inaccurate as mass increases.

Although one can determine a DNA piece with a length of 20 to 25 bases (around 6,000 to 8,000 atomic mass units) accurately to within three to five atomic mass units, it is no longer the case for DNA having a length of about 40 to 50 bases (around 12,000 to 16,000 atomic mass units). In the latter case the mass difference has to be about 40 to 60 mass units to ensure reliable differentiation. The four natural nucleobases of DNA, however, only have mass differences of 9 to a maximum of 40 atomic mass units so a base exchange can no longer be reliably detected at this length of DNA pieces. Only with extremely careful work and extremely efficient cleaning to keep adduct formation to a minimum is it possible to detect mass differences of 20 atomic mass units in this mass range.

The minimum length of a PCR amplified DNA product around an SNP (single nucleotide polymorphism) is about 40 to 50 bases because two primers with a length of 20 bases have to be used and the primers can sometimes not be connected to the SNP point directly. For these PCR products there is therefore no longer any reliable mass-spectrometric detection of a base exchange by MALDI ionization, which is otherwise so convenient and fast.

Recently a method of mutation diagnostics became known which uses MALDI mass spectrometry and which can be particularly used for SNP analysis (Little, D. P., Braun, A., Darnhofer-Demar, B., Frilling, A., Li, Y., Mclver, R. T. and Köster, H.; Detection of RET proto-oncogene codon 634 mutations using mass spectrometry. J. Mol. Med. 75, 745–750, 1997). Initially a normal PCR is performed with a pair of first primers in order have sufficient DNA material available for further steps. After an intermediate cleaning procedure to remove residual primers and nucleoside triphosphates a new primer is added. This second primer is synthesized so that it becomes attached to the matrix strand in the vicinity of a known point mutation or of an SNP. Between the position of this SNP and the 3' end of the primer (the primer is extended at that end) the sequence of the matrix strand may contain a maximum of three of the four nucleobases. The fourth base occurs at the point of the SNP at the earliest (of the polymorphism in the case of allele 1) or after it (allele 2) for the first time. With a polymerase and the special set of deoxynucleoside triphosphates (the maximum of three complementary ones which occur up to polymorphism) and a dideoxynucleoside triphosphate (with the base which is complementary to the allele of the polymorphism) the primer is then extended by copying. The dideoxynucleoside triphosphate terminates the chain extension. Depending on the allele of the polymorphism the chain extension is terminated at the SNP or several nucleotides later. This method has been termed by the authors "PROBE".

The method is very favorable because it ends with short DNA products with a length of about 25 nucleotides, which are very suitable for MALDI analysis, and because the mass difference is always at least one base. However, on the other hand it calls for a larger number of thermal and cleaning phases. Initially the PCR products must be cleaned of the first primer, enzyme and all nucleoside triphosphates, whereby one must take into consideration that the purification, particularly of primer, becomes increasingly difficult, the shorter the DNA product is. Only then can the second primer which is to be lengthened be added with the special set of nucleoside triphosphates. Now new thermal cycles have to be integrated to extend the primer. Then there has to be a cleaning phase before the extension product can be measured with MALDI. The authors have solved the problem of these phases by fixing the DNA to a surface not only by physical absorptive means but also chemically, but must detach it later, which complicates the reactions again though.

SUMMARY OF THE INVENTION

The invention consists of changing the mass of at least one of the four nucleoside triphosphates used in PCR amplification by a chemical change (derivatizing) in such a way that, on the one hand, the PCR reaction is not disturbed, but on the other hand, a base exchange becomes reliably detectable due to the then considerably changed mass of the PCR product. The decision as to which nucleoside triphosphate is best used with changed mass depends on the type of the base exchange.

Derivatization tends to lead to a mass enlargement rather than a reduction. In the case of the nucleoside triphosphate G this enlargement only needs to be about 14 atomic mass units in order to detect the base reliably in an exchange by one of the two lightest nucleoside triphosphates (C and T). However, a mass difference of at least 20 atomic mass units is better; and 40 to 80 atomic mass units as derivatization increase are ideal for this method.

Changed-mass nucleoside triphosphates are not even required for all the four bases. Two changed-mass nucleoside triphosphates are adequate for detecting all the base exchanges because the bases in the DNA strand and counter strand always occur in pairs (G and C, A and T). Favorably the masses of the two heaviest nucleoside triphosphates (G and A) must be enlarged. However, the mass change only needs to be detectable in one strand. Normally (if no special measures are taken) both strands are always measured simultaneously in the MALDI process. If only one strand is used (there are also methods for this) the strand used for measurement can be selected accordingly.

The nucleobases consist of the two purins, adenine (A) and guanine (G) and the two pyrimidines cytosine (C) and thymine (T). (In the RNA the uracil (U) occurs instead of the thymine). For structural reasons G and A can be more easily derivatized according to current knowledge, and this is more favorable for the invention in any case. Derivatization of the pyrimidines is not precluded though.

In particular it is a basic idea of the invention to derivatize purines A and G in position 7 (letters b and e in FIG. 1). For this it is necessary to replace the nitrogen atoms of position 7 by methine groups. The result is 7-desaza-purine nucleosides which are then transformed into triphosphates. The C-atom hydrogen in position 7 is then replaced by a correspondingly heavy group. Very different groups can be used. Particularly the modified purine nucleosides in position 7 can be derivatized by attaching remainders of the form —R, —$(CH_2)_n$—R or —C≡C—R, whereby R can be a remainder of the form —H, —F, —Cl, —Br, —I, —OH, —SH, —SeH, -alkyl, -alkenyl, -alkinyl, —$OCH_3$, —$SCH_3$, —$CHF_2$, —$CF_3$, —$CH_2CH_2$—$(OCH_2CH_2)_n$—O-alkyl, —$NH_2$, —$(NHCOCH_2)_n$—$NH_2$, —$(NHCOCH_3)_n$— $NH_2$, —$OCOCH_2NH_2$, —$OCOCH_2(NHCOCH_2)_n$—$NH_2$— $OCOCHCH_3NH_2$, —$OCOCHCH_3(NHCOCH_3)_n$—$NH_2$, —$OCH_2F$, —$OCHF_2$, $OCF_3$, —$SCH_2F$, —$SCHF_2$ or —$SeCH_3$ inasmuch as this produces a mass difference of at least 14 atomic mass units, although at least 20 or even 40 atomic mass units are preferable. Furthermore, the specialist will be aware of further residues which fulfill the same purpose.

There is also the possibility of derivatizing 8-aza-7-desaza-purine nucleosides as described above. Position 6 of the guanine, to which an oxygen atom is normally attached, can also be derivatized for mass modification. In this way it is possible to integrate a sulfur or selenium atom without essentially disturbing the Watson-Crick bond with the opposite pyrimidine base.

For mass modification O1' can be substituted by S1' in the deoxyribose. A DNA building block can also be replaced by a phosphothioate.

It is a further basic idea of the invention to manufacture appropriate chemical kits for this SNP analysis. These can, on the one hand, contain only the modified nucleoside triphosphates, for example in compounds with unmodified nucleoside triphosphates. However, buffers, activators for the polymerase, and stabilizers, may also be included. It is also possible, though, to manufacture ready-to-use kits which also already contain the inactivated polymerase and to which only the specific primers and activators have to be added in use.

DESCRIPTION OF THE PREFERRED EMBODIMENTS

Figure 1:
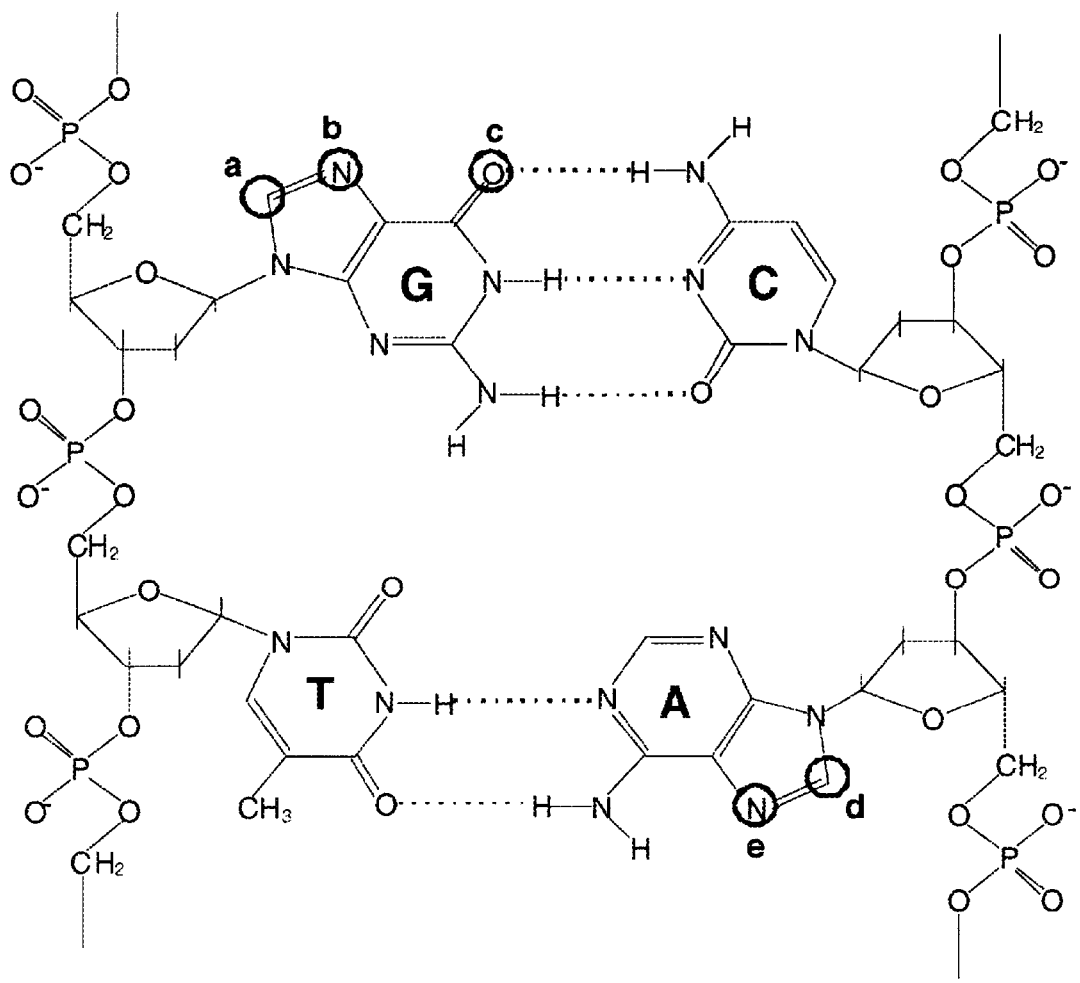
FIG. 1 shows a section of a genomic double strand with the four bases A, C, G, and T bonded in pairs in accordance with Watson-Crick (two or three hydrogen bridge bonds). Position 7, which is particularly suitable for a derivatization of 7-desaza nucleotides, is referred to by the letter b on guanine G, and by the letter e on the adenosine A. Letters a and d designate the preferably azalated positions 8 of the two purines G and A. Letter c designates the oxygen in position 6 of the guanine, which can be replaced by sulfur or selenium.
Figure 2:
FIG. 2 shows the 7-desaza-purine nucleosides and their possible derivatizations for mass modification. The numbers 1, 3, 5, 7, and 9 indicate the purine atoms of the ring system in the so-called "purine count" usually applied.

A particularly favorable embodiment is the derivatization of an 8-aza-7-desaza-guanine nucleoside triphosphate at position 7 with a —C≡C—CH$_2$NH$_2$ group (propargylamino group). Consequently the base guanine becomes 53 atomic mass units heavier. Since the base guanine is already 40 atomic mass units heavier than the lightest base, cytosine, and 16 atomic mass units heavier than the next heavier base, adenine, a base exchange involving the guanine is very easy to detect by mass spectrometry, even if conditions cannot always be ideal for mass spectrometry.

However, a derivatization of the same position with an ethinyl group —C≡CH already also leads to a normally differentiable situation. Although the mass difference here is only 23 atomic mass units because guanine is already 40 atomic mass units heavier than the lightest base, this difference can be reliably detected if the mass spectrometry is performed with some care.

Furthermore, a bromination at position 7 of 8-aza-7-desaza-guanine nucleoside triphosphate is favorable. This produces a mass increase of about 80 atomic mass units. The fact that bromium consists of two isotopes is not important—with this type of analysis they cannot be resolved by mass spectrometry.

Such a mass difference of about 80 atomic mass units is ideal for the present purpose. The average mass of a nucleotide, which is normally about 310 atomic mass units, is thereby increased to about 330 mass units. The mass increase of a base should preferably remain below 80 to 120 atomic mass units because otherwise the possibilities of the method for multiplexing are restricted.

Multiplexing consists of analyzing in one PCR step not only an SNP but also several SNPs due to several primer pairs. For this it is necessary to plan the masses of the resulting product so that the resulting mass ranges of the two alleles of the various SNPs do not overlap.

The method according to this invention provides major advantages over all the other methods known so far:

1. The method is uniquely simple; all that is necessary is a single PCR replication, cleaning once, and then analysis by mass spectrometry.
2. Compared with other methods the cleaning is much simpler because large double-strand DNA products have to be cleaned. Even the further elimination of the primers is simpler (although it is not absolutely necessary) because the mass difference is important. An example of a cleaning method which can be used is purification in pipette syringes (reversed phase chromatography). Such pipette syringes are already commercially available. However, purification by targeted adsorption on magnetic beads can be used, for which there is commercial apparatus that can be integrated into automatic pipetting machines.

Consequently an automation of sample preparation for a MALDI or also ESI mass spectrometry is easy to achieve. There are already pipetting robots with integrated thermocyclers for performing the PCR. Automation is highly desirable for the analysis of SNPs because generally tens of thousands of samples have to be analyzed for genotyping, particularly for coupling analysis of diseases with gene loci and for statistical biological information technology.

The types of mass-changing derivatization are not given in full here. The specialist, and in particular the biochemical synthesist, can easily define other derivatization options based on the idea of the invention which conform to the purpose of the invention.

What is claimed is:

1. Method of mass-spectrometric analysis of known polymorphisms or mutations in genomic DNA, with selective replication of short DNA strands by PCR amplification covering the polymorphous position, the method comprising:

combining the genomic DNA with nucleoside triphosphates, the mass of at least one of which is altered by a chemical change, wherein altering the mass of a nucleoside triphosphate comprises using modified 7-desaza-purine nucleoside triphosphates or 8-aza-7-desaza-purine nucleoside triphosphates;

performing a PCR amplification that incorporates the nucleotide triphosphates into replications of the genomic DNA; and analyzing the replicated DNA with a mass spectrometer.

2. Method as in claim 1, wherein the 7-desaza-purine nucleoside triphosphates or 8-aza-7-desaza-purine nucleoside triphosphates are derivatized at position 7 of at least one of guanine and adenine.

3. Method as in claim 2, wherein the modified purine nucleoside triphosphates are derivatized at position 7 by attachment of a material described by —R, —(CH$_2$)$_n$—R or —C≡C—R, whereby R designates a remainder of the form —H, —F, —Cl, —Br, —I, —OH, —SH, —SeH, -alkyl, -alkenyl, -alkinyl, —CHF$_2$, —CF$_3$, —OCH$_3$, —OCH$_2$F, —OCHF$_2$, —OCF$_3$, —SCH$_3$, —SCH$_2$F, —SCHF$_2$, —(OCH$_2$CH$_2$)$_n$—O-alkyl, —NH$_2$, —(NHCOCH$_2$)$_n$—NH$_2$, —(NHCOCHCH$_3$)$_n$—NH$_2$, —OCOCH$_2$NH$_2$, —OCOCH$_2$(NHCOCH$_2$)$_n$—NH$_2$, —OCOCHCH$_3$(NHCOCH$_3$)$_n$—NH$_2$, —OCOCHCH$_3$—NH$_2$, or —SeCH$_3$.

4. Method as in claim 1 wherein the altered nucleoside triphosphate includes guanine, and oxygen at position 6 of the guanine is replaced by sulfur or selenium.

5. Method of mass-spectrometric analysis of known single nucleotide polymorphisms in genomic DNA, with selective replication of short DNA strands by PCR amplification covering the polymorphous position, the method comprising:

combining the genomic DNA with nucleoside triphosphates, the mass of at least one of which is altered by a chemical change, the alteration comprising derivatizing the deoxyribose unit of a nucleoside triphosphate by replacing at least one chemical component of the unit with at least one different chemical component of different mass;

performing a PCR amplification that incorporates the nucleotide triphosphates into replications of the genomic DNA that span the single nucleotide polymorphism positions; and analyzing the replicated DNA with a mass spectrometer.

6. Method of mass-spectrometric analysis of known polymorphisms or mutations in genomic DNA, with selective replication of short DNA strands by PCR amplification covering the polymorphous position, the method comprising:

combining the genomic DNA with nucleoside triphosphates, the mass of at least one of which is altered by a chemical change, wherein an altered nucleoside triphosphate is derivatized at its α-phosphor atom by replacing a substituent at the α-phosphor atom with at least one different chemical component of different mass;

performing a PCR amplification that incorporates the nucleotide triphosphates into replications of the genomic DNA; and analyzing the replicated DNA with a mass spectrometer.

7. Chemical kit apparatus for use in preparing a genomic DNA sample for mass-spectrometric analysis of known polymorphisms or mutations by a method that includes the selective replication of short DNA strands by PCR amplification covering the polymorphous position, the apparatus comprising:

a set of nucleoside triphosphates for use during the PCR amplification wherein at least one of the nucleoside triphosphates has been altered such that the deoxyribose unit of the altered nucleoside triphosphate is derivatized by replacing at least one chemical component of the unit with at least one different chemical component of different mass.

8. Chemical kit apparatus as in claim 7, wherein the kit apparatus comprises all the enzymes, buffers, activators, and modified and unmodified nucleoside triphosphates required for the PCR.

9. Chemical kit apparatus for use in preparing a genomic DNA sample for mass-spectrometric analysis of known polymorphisms or mutations by a method that includes the selective replication of short DNA strands by PCR amplification covering the polymorphous position, the apparatus comprising:

a set of nucleoside triphosphates for use during the PCR amplification wherein at least one of the nucleoside triphosphates has been altered, the alteration comprising using modified 7-desaza-purine nucleoside triphosphates or 8-aza-7-desaza-purine nucleoside triphosphates.

* * * * *